(12) United States Patent
Summers et al.

(10) Patent No.: US 10,519,108 B2
(45) Date of Patent: Dec. 31, 2019

(54) INHIBITORS OF RETINALDEHYDE DEHYDROGENASES AND METHODS OF USE

(71) Applicant: The Board of Regents of the University of Oklahoma, Norman, OK (US)

(72) Inventors: Jody A. Summers, Edmond, OK (US); Angelica R. Harper, Norman, OK (US); Tim Mather, Oklahoma City, OK (US); Anthony Burgett, Norman, OK (US); Anh Thi Quynh Le, Norman, OK (US)

(73) Assignees: The Board of Regents of the University of Oklahoma, Norman, OK (US); Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 15/758,555

(22) PCT Filed: Sep. 16, 2016

(86) PCT No.: PCT/US2016/052170
§ 371 (c)(1),
(2) Date: Mar. 8, 2018

(87) PCT Pub. No.: WO2017/049110
PCT Pub. Date: Mar. 23, 2017

(65) Prior Publication Data
US 2018/0258037 A1    Sep. 13, 2018

Related U.S. Application Data

(60) Provisional application No. 62/220,022, filed on Sep. 17, 2015.

(51) Int. Cl.
*C07C 403/16* (2006.01)

(52) U.S. Cl.
CPC ........ *C07C 403/16* (2013.01); *C07C 2601/16* (2017.05)

(58) Field of Classification Search
CPC .................................................. C07C 403/16
See application file for complete search history.

(56) References Cited

U.S. PATENT DOCUMENTS

| | | | |
|---|---|---|---|
| 5,449,844 A * | 9/1995 | Ancel | C07C 45/511 568/378 |
| 9,078,852 B2 * | 7/2015 | Plutzky | A61K 31/11 |
| 2003/0119715 A1 | 6/2003 | Ward et al. | |
| 2007/0189984 A1 | 8/2007 | Wolber et al. | |
| 2011/0046234 A1 | 2/2011 | Plutzky et al. | |

OTHER PUBLICATIONS

PCT/US2016/052170; "International Search Report and Written Opinion"; dated Feb. 3, 2017; 13 pages.

* cited by examiner

*Primary Examiner* — Golam M Shameem
(74) *Attorney, Agent, or Firm* — Hall Estill Law Firm

(57) ABSTRACT

Compounds having inhibitory activity against retinaldehyde dehydrogenases (RALDHs). The compounds can be used, for example, to inhibit synthesis of retinoic acid for the treatment of refractive error disorders such as myopia, and as infertility treatments by inhibiting spermatogenesis.

15 Claims, 2 Drawing Sheets

INHIBITORS OF RETINALDEHYDE DEHYDROGENASES AND METHODS OF USE

CROSS-REFERENCE TO RELATED APPLICATIONS

The present application is a national stage application of a PCT application having International Application No. PCT/US2016/052170, filed Sep. 16, 2016, which claims priority to U.S. Provisional Application having U.S. Ser. No. 62/220,022, filed Sep. 17, 2015, which claims the benefit under 35 U.S.C. 119(e), the disclosure of which is hereby expressly incorporated herein by reference.

BACKGROUND

Aldehyde dehydrogenases (ALDHs) comprise a superfamily of 19 enzymes that catalyze the irreversible oxidation of various aldehydes to their corresponding carboxylic acids. This class includes the retinaldehyde dehydrogenases (RALDHs). The three class one (cytosolic) ALDHs that synthesize retinoic acid (ALDH1A1, ALDH1A2, and ALDH1A3; a.k.a., respectively, RALDH1, RALDH2, and RALDH3) are involved in growth and development of many major organ systems. There have been no specific inhibitors for the class one ALDH enzymes. Disulfiram, citral, and DEAB have been used to inhibit retinoic acid synthesis in experimental settings, but they demonstrate poor isoform selectivity resulting in numerous off target effects.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the present disclosure.

DETAILED DESCRIPTION

Figure 1:
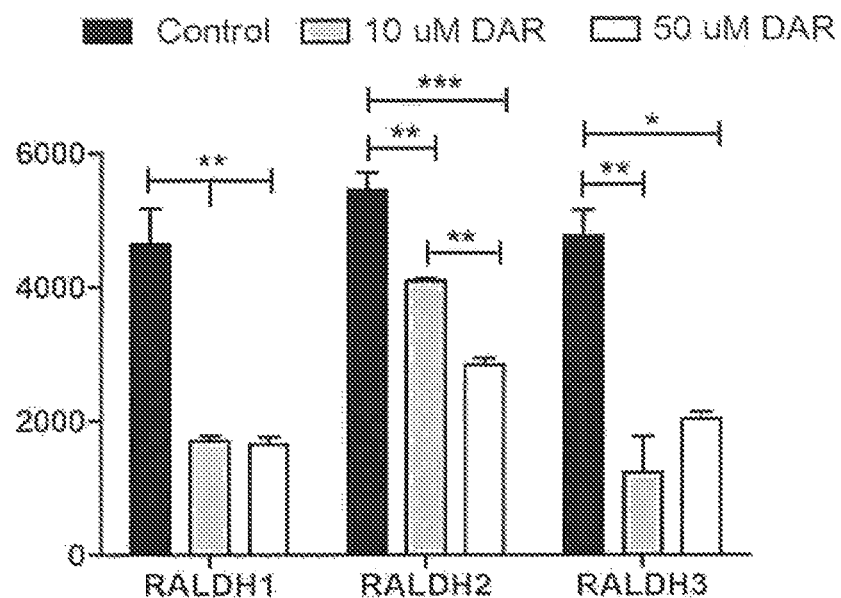
FIG. 1 shows the activity of retinaldehyde dehydrogenase 1, 2, and 3 (RALDH1, RALDH2, and RALDH3) in the presence of the compound Dichloro-all-trans-retinone (DAR) as assessed by NADH synthesis, measured using a fluorescence-based NADH sensor. DAR effectively inhibits RALDH1, RALDH2 and RALDH3. $*p \leq 0.05$, $p \leq 0.01$, $*p \leq 0.001$, one-way ANOVA with Bonferroni correction.
Figure 2:
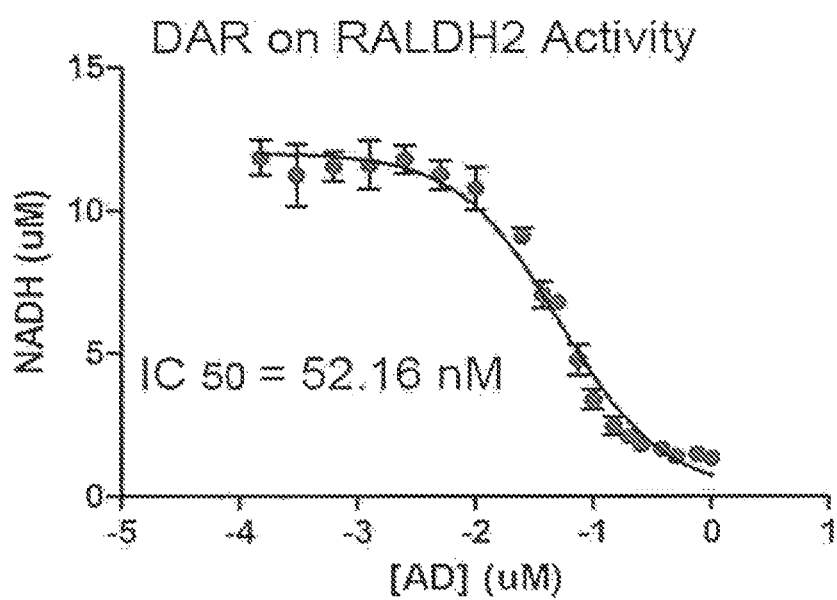
FIG. 2 shows the activity of RALDH2 in the presence of DAR as assessed by NADH synthesis (μM), measured using a fluorescence-based NADH sensor. DAR inhibits RALDH2 in a dose-dependent manner with an $IC_{50}=52.16$ nM (95% C.I.=41.0-66.4 nM). $*p \leq 0.05$, $p \leq 0.01$, $*p \leq 0.001$, ANOVA.
Figure 3:
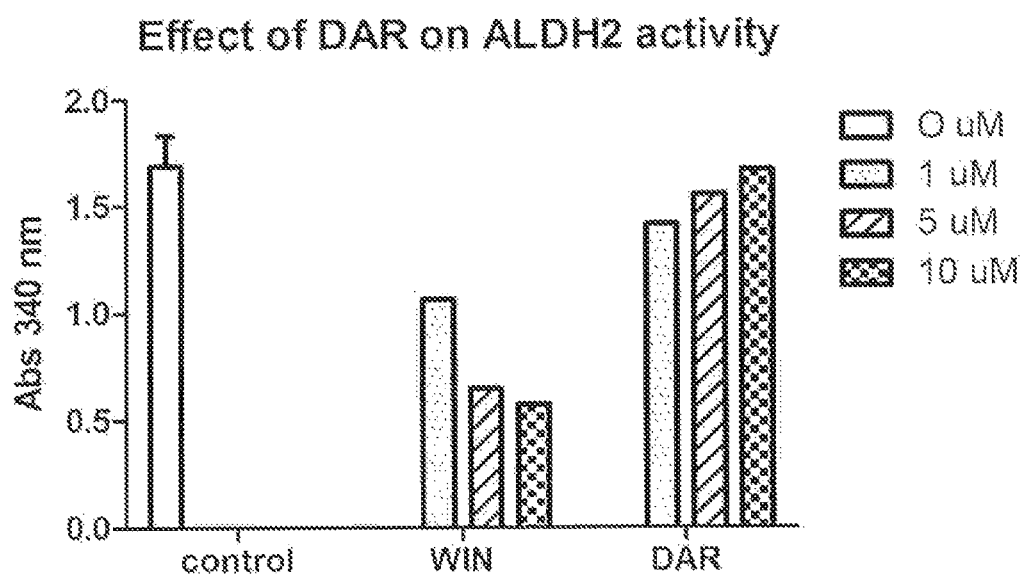
FIG. 3 shows the effect of DAR on aldehyde dehydrogenase 2 (ALDH2) as assessed by NADH synthesis as measured by absorbance at 340 nm. DAR does not significantly inhibit ALDH2, in contrast to the non-specific ALDH2 inhibitor compound WIN-18446 (WIN). $*p \leq 0.05$, $p \leq 0.01$, $*p \leq 0.001$, ANOVA.
Figure 4:
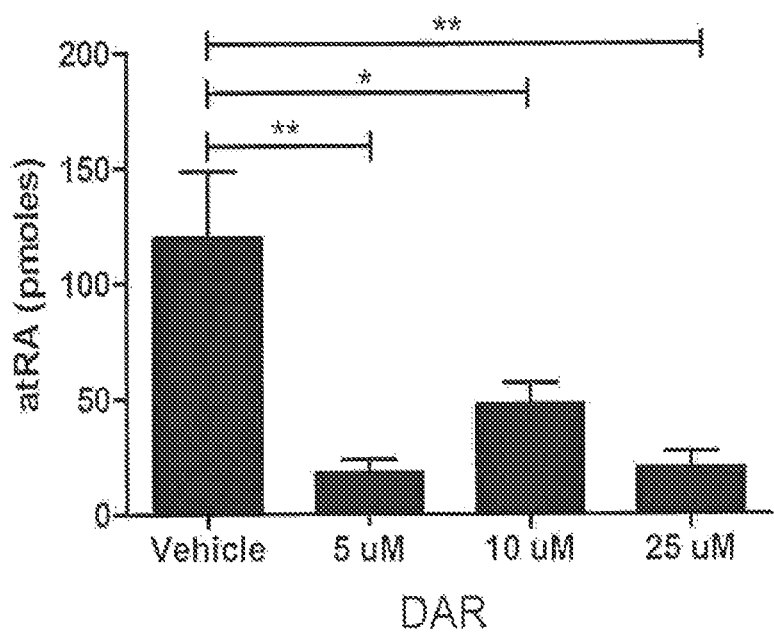
FIG. 4 shows that DAR is an effective RALDH inhibitor in recovering choroid tissue homogenates. RALDH activity was assessed in choroid tissue homogenates in the presence of DAR (5-25 μM), or vehicle (EtOH) by measuring all-trans-retinoic acid (atRA) synthesis. Choroid cytosol fractions were incubated in the presence of cofactor NAD (4 mM) and all-trans-retinaldehyde (25 μM) at 37° C. for 30 min. Following incubation, retinoids were extracted and quantified using HPLC. Retinoic acid synthesis by RALDH was significantly inhibited following incubation with DAR. $*p \leq 0.05$, $**p \leq 0.01$, one-way ANOVA with Bonferroni correction.

The present disclosure describes novel compounds which selectively target the three RALDH isoforms (RALDH1, RALDH2, and RALDH3), enabling the inhibition of retinoic acid synthesis while leaving unaffected the functions of the other ALDHs, some of which are critical for normal cellular homeostatsis or for alcohol detoxification (i.e., ALDH2). Pharmacological inhibitors have been developed for three of the 19 ALDH isozymes: ALDH2, ALDH1A1 (RALDH1), and ALDH3A1. However, prior to the present work, there have been no inhibitors specific for the three RALDH isoforms. The development of a class of RALDH isoform-specific inhibitors enables, for the first time, modulation of endogenous retinoic acid synthesis without affecting enzymes that are critical for certain life processes and detoxification.

Before further describing various embodiments of the present disclosure in more detail by way of exemplary description, examples, and results, it is to be understood that the inventive concepts of the present disclosure are not limited in application to the details of methods and compositions as set forth in the following description. The embodiments of the present disclosure are capable of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure ma y be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts. All such similar substitutes and modifications apparent to those having ordinary skill in the art are deemed to be within the spirit, scope, and concept of the inventive concepts as defined herein.

As utilized in accordance with the methods and compositions of the present disclosure, the following words and terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only, or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100 and 1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include"), and "containing" (and any form of containing, such as "contains" and "contain") are inclusive or open-ended and do not exclude additional, unrecited elements or method steps.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "active agent" or "active agent(s)" as used herein refers to RALDH inhibitors as described, disclosed, or supported herein.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±15%, ±10%, or ±9%, or ±8%, or ±7%, or ±6%, or ±5%, or ±4%, or ±3%, or ±2%, or ±1%, or ±0.5%, or ±0.1% from the specified value, as such variations are appropriate to perform the disclosed methods and as understood by persons having ordinary skill in the art.

As used herein, the term "substantially" means that the subsequently described event, circumstance, or object completely occurs, or that the subsequently described event, circumstance, or object occurs to a great extent or degree. For example, the term "substantially" can mean that the subsequently described event or circumstance occurs at least 90% of the time, or at least 95% of the time, or at least 98% of the time, or the event or object is present in at least 90%, 95%, or 98% of the cases.

As used herein, all numerical values or ranges include fractions of the values and integers within such ranges and fractions of the integers within such ranges unless the context clearly indicates otherwise (e.g., when used in reference to the number of amino acid residues in a peptide). Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The term "ophthalmically-acceptable" refers to compounds and compositions which are suitable for administration to the eyes of humans and/or animals without undue adverse side effects such as toxicity, irritation and/or allergic response commensurate with a reasonable benefit/risk ratio.

By "biologically active" is meant the ability of a compound to modify the physiological system of a cell or an organism without reference to how the compound has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 75 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 75% (w/w) pure, or at least 80% (w/w) pure, or at least 85% (w/w) pure, or at least 90% (w/w) pure, or at least 91% (w/w) pure, or at least 92% (w/w) pure, or at least 93% (w/w) pure, or at least 94% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal or an avian species. Non-limiting examples of animals within the scope and meaning of this term include dogs, cats, rats, mice, guinea pigs, chinchillas, horses, goats, cattle, sheep, chickens, turkeys, ducks, geese, zoo animals, Old and New World monkeys, non-human primates, and humans, and any other animal which could demonstrate an effect from treatment with the active agents of the present disclosure.

"Treatment" refers to therapeutic treatments. "Prevention" refers to prophylactic or preventative treatment measures. The term "treating" refers to administering the composition to a patient for therapeutic purposes. The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable result or therapeutic effect without excessive adverse side effects (such as toxicity, irritation and allergic response) commensurate with a reasonable benefit/risk ratio when used in the manner of the inventive concepts. The term "effective amount" refers to an amount of an active agent which is sufficient for controlling, reducing, or inhibiting a disorder or condition described herein, or sufficient for effecting a desirable result. The term "controlling" is intended to refer to all processes wherein there may be a slowing, interrupting, arresting, or stopping of the progression of the disorder or condition and does not necessarily indicate a total elimination of the symptoms. The effective amount for a patient will depend upon the type of patient, the patient's size and health, the nature and/or severity of the condition to be treated, the method of administration, the duration of treatment, the nature of concurrent therapy (if any), the specific formulations employed, and the like. Thus, it is not possible to specify herein an exact effective amount in advance. However, the effective amount for a given situation can be determined by one of ordinary skill in the art using routine experimentation based on the information provided herein.

More particularly, in at least one embodiment, an effective amount of an active agent of the present disclosure refers to an amount which is effective in controlling, reducing, or inhibiting an RALDH, synthesis of retinoic acid, myopia, or spermatogenesis in an individual. For example, the term "controlling" is intended to refer to all processes wherein there may be a slowing, interrupting, arresting, or stopping of the progression of myopia and does not necessarily indicate a total elimination of myopia in the subject receiving the treatment.

The term "effective amount" is further meant to define an amount resulting in the improvement of any parameters or clinical symptoms characteristic of myopia in a subject. The actual dose will vary with the patient's overall condition, the seriousness of the symptoms, and counter indications. As used herein, the term "effective amount" also means the total amount of each active component of the pharmaceutical composition or method that is sufficient to show a meaningful patient benefit, i.e., reduction of an ocular refractive error disorder (e.g., myopia) and/or spermatogenesis. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, e.g., myopia, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, e.g., myopia, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

In at least certain embodiments, the active agent(s) of the present disclosure may be used as a pharmaceutical composition when combined with a pharmaceutically acceptable carrier. Such a composition may contain, in addition to the active agent and carrier, diluents, fillers, salts, buffers, stabilizers, solubilizers, and other materials well known in the art. Suitable carriers, vehicles and other components of the formulation are described, for example, in *Remington: The Science and Practice of Pharmacy*, 21$^{st}$ ed. The term "pharmaceutically acceptable" means a non-toxic material that does not interfere with the effectiveness of the biological activity of the active agent. The characteristics of the carrier will depend on the route of administration.

In certain embodiments, the pharmaceutical compositions of the present disclosure may be in the form of liposomes in which the active agent(s) is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

An effective amount of the active agent used in the treatment described herein can be determined by the attending diagnostician, as one skilled in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific condition involved; the degree of or involvement or the severity of the condition; the response of the individual subject; the particular compound administered; the mode of administration; the bioavailability characteristic of the preparation administered; the dose regimen selected; the use of concomitant medication; and other relevant circumstances.

As used herein, a "pharmaceutically-acceptable carrier, vehicle, diluent, or excipient" may also refer to a pharmaceutically-acceptable solvent, suspending agent or material for delivering the active agent(s) of the present disclosure to the subject. "Ophthalmically-acceptable vehicle, carrier, diluent, or excipient" is an ophthalmically-acceptable solvent, suspending agent, or material for delivering the active agents of the present disclosure to an eye of the subject. The carrier may be liquid or solid and is selected with the planned manner of administration in mind. Examples of pharmaceutically-acceptable vehicles, carriers, diluents, or excipients, and/or ophthalmically-acceptable vehicles, carriers, diluents, or excipients that may be utilized in accordance with the present disclosure include, but are not limited to, polyethylene glycol (PEG), polymers, carboxymethylcellulose, liposomes, ethanol, DMSO, aqueous buffers, saline solutions, solvents, oils, DPPC, lipids, and combinations thereof. Other examples include, but are not limited to, biocompatible hydrogels, bandages, and contact lenses, which can also be coated with the active agent and placed directly on the eye.

Non-limiting examples of modes of administration include oral, topical, retrobulbar, subconjunctival, intraocular, periocular, transdermal, parenteral, subcutaneous, intranasal, intramuscular, intraperitoneal, intravitreal, and intravenous routes, including both local and systemic applications. The term "topical" as used herein to define a mode of administration, means that a material is administered by being applied to an epithelial surface or tissue. In addition, as noted, the compositions of the present disclosure may be designed to provide delayed, controlled, extended, and/or sustained release using formulation techniques which are well known in the art.

As used herein, the term "concurrent therapy" is used interchangeably with the terms "combination therapy" and "adjunct therapy," and will be understood to mean that the subject in need of treatment is treated or given another drug for the condition in conjunction with the pharmaceutical compositions of the present disclosure. This concurrent therapy can be sequential therapy, where the patient is treated first with one composition and then the other composition, or the two compositions are given simultaneously.

In certain non-limiting embodiments, an effective amount or therapeutic dosage of a pharmaceutical composition of the present disclosure contains, sufficient active agent to deliver from about 0.001 µg/kg to about 100 mg/kg (weight of active agent/body weight of the subject). For example, the composition will deliver about 0.01 µg/kg to about 50 mg/kg, and more particularly about 0.1 µg/kg to about 10 mg/kg, and more particularly about 1 µg/kg to about 1 mg/kg. Practice of a method of the present disclosure may comprise administering to a subject an effective amount of the active agent in any suitable systemic and/or local formulation, in an amount effective to deliver the therapeutic dosage of the active agent. In certain embodiments, an effective dosage may be, in a range of about 1 µg/kg to about 1 mg/kg of the active agent.

As noted above, administration of the active agent of the present disclosure can be carried out in a variety of conventional ways, such as, but not limited to, orally, by inhalation, rectally, or by cutaneous, subcutaneous, intraperitoneal, vaginal, or intravenous injection. Oral formulations may be formulated such that the active agent passes through a portion of the digestive system before being released, for example it may not be released until reaching the small intestine, or the colon. The dosage can be administered, for example but not by way of limitation, on a one-time basis, or administered at multiple times (for example but not by way of limitation, from one to five times per day, or once or twice per week).

When a pharmaceutical composition containing the active agent is administered orally, the composition may be in the form of a tablet, capsule, lozenge, melt, powder, suspension, solution, emulsion, or elixir. The pharmaceutical composition may additionally contain a solid carrier such as a gelatin or an adjuvant. Solid unit dosage forms can be capsules of the ordinary gelatin type containing, for example, surfactants, lubricants and inert fillers such as lactose, sucrose, and cornstarch or they can be sustained release preparations. The dosage may contain from about 0.001 to 95% of the active agent by weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, 35 propylene glycol or polyethylene glycol. When administered in liquid form, the pharmaceutical composition may contain from about 0.005 to 95% by weight of active agent. For example, a dose of 10-1000 mg of the pharmaceutical composition could be administered orally once to twice a day. Ultimately, the attending physician will decide the amount of active agent(s) with which to treat each individual patient.

In another embodiment, the active agent(s) of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active agent(s) in an aqueous or non-aqueous pharmaceutically acceptable solvent which may also contain suspending agents, sweetening agents, flavoring agents, and preservative agents as are known in the art.

For parenteral administration, for example, the active agent(s) may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin.

The pharmaceutical carrier may also contain stabilizers, preservatives, buffers, antioxidants, or other additive known to those of skill in the art.

When an effective amount of the active agent(s) is administered by intravenous, cutaneous or subcutaneous injection, the active agent(s) may be in the form of a pyrogen-free, parenterally-acceptable aqueous solution or suspension. The preparation of such solutions or suspensions, having due regard to pH, isotonicity, stability, and the like, is within the skill in the art. A particular pharmaceutical composition for intravenous, cutaneous, or subcutaneous injection may contain, in addition to the active agent(s), an isotonic vehicle such as Sodium Chloride Injection, Ringer's Injection, Dextrose Injection, Dextrose and Sodium Chloride Injection, Lactated Ringer's Injection, or other vehicle as known in the art.

As noted above, the compositions can also include an appropriate carrier. For topical use, any of the conventional excipients may be added to formulate the active agent(s) into a lotion, ointment, powder, cream, spray, or aerosol. For surgical implantation, the active agent(s) may be combined with any of the well-known biodegradable and bioerodible carriers, such as polylactic acid and collagen formulations. Such materials may be in the form of solid implants, sutures, sponges, wound dressings, and the like. Preparation of such compositions for local use is detailed in *Remington: The Science and Practice of Pharmacy*, 21$^{st}$ ed.

As noted, particular amounts and modes of administration are able to be determined by one skilled in the art. One skilled in the art of preparing formulations can readily select the proper form and mode of administration depending upon the particular characteristics of the active agent(s) selected a nd the condition to be treated, and other relevant circumstances, using formulation technology known in the art, described, for example, in *Remington: The Science and Practice of Pharmacy*, 21$^{st}$ ed. The pharmaceutical compositions of the present disclosure can be manufactured utilizing techniques known in the art.

Additional pharmaceutical methods may be employed to control the duration of action of the active agent(s). Increased half-life and controlled release preparations may be achieved through the use of polymers to conjugate, complex with, absorb, or contain the active agent(s) described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, proteins (e. g., bovine serum albumin or human serum albumin) and the appropriate concentration of macromolecules as well as the methods of incorporation, in order to control release.

Another possible method useful in controlling the duration of action by controlled release preparations and half-life is incorporation of the active agent(s) into particles of a polymeric material such as polyesters, polyamides, polyamino acids, hydrogels, poly(lactic acid), ethylene vinylacetate copolymers, copolymer micelles of, for example, polyethylene glycol (PEG) and poly(l-aspartamide).

It is also possible to entrap the active agent(s) in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the active agent(s) is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

The active agent(s) of the present disclosure can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the active agent(s) of the present disclosure may be incorporated into pharmaceutical preparations which may be used for therapeutic purposes. However, the term "pharmaceutical preparation" is intended in a broader sense herein to include preparations containing active agent(s) in accordance with present disclosure, used not only for therapeutic purposes but also for reagent or diagnostic purposes as known in the art. The pharmaceutical preparation intended for therapeutic use should contain a "pharmaceutically acceptable" or "effective amount" of the active agent(s), i.e., that amount necessary for a therapeutic response in a patient or subject in need of such treatment. If the pharmaceutical preparation is to be employed as a reagent or diagnostic, then it should contain reagent or diagnostic amounts of the active agent(s).

Various embodiments of the present disclosure will be more readily understood by reference to the following examples and description, which as noted above are included merely for purposes of illustration of certain aspects and embodiments of the present disclosure, and are not intended to be limiting. The following detailed examples and methods describe how to make and use compounds and compound-containing compositions of the present disclosure and are to be construed, as noted above, only as illustrative, and not limitations of the disclosure in any way whatsoever. Those skilled in the art will promptly recognize appropriate variations from the materials and procedures described herein.

The compounds (active agents) of the present disclosure have applications to several areas of human health (as well as the health and development of other mammalian and avian species having biopathways involving retinoic acid synthesis). Recently, retinoic acid has been shown to play a role in the regulation of postnatal eye growth and the development of myopia. The synthesis of all-trans-retinoic acid (atRA) by the choroid (the vascular layer between the retina and sclera) plays a role in postnatal control of eye size. Choroidal synthesis of atRA is modulated during periods of visually-induced changes in ocular growth and has pronounced effects on scleral extracellular matrix metabolism in chicks, guinea pigs, and primates. We recently determined that of all atRA-metabolizing enzymes examined, only retinaldehyde dehydrogenase 2 (RALDH2) was modulated during periods of visually guided eye growth in chicks. Moreover, we demonstrated that atRA concentrations generated by choroidal RALDH2 activity are sufficient to significantly affect scleral ECM remodeling, resulting in changes in the rate of ocular growth and refraction. These results provided the first direct evidence of a gene expressed in the choroid that is regulated by visual stimuli AND can modulate scleral ECM remodelling. Based on these results, RALDH2 was determined to be a target for the development of pharmacologic strategies to slow or prevent the development of myopia in children. Specific modulation of retinoic acid synthesis in the eye therefore has applications for the treatment refractive error disorders (e.g. myopia, hyperopia) by controlling postnatal axial elongation. Thus, in at least one embodiment, the novel compounds disclosed herein can be used to inhibit or treat myopia.

Myopia is the leading cause of visual impairment in the world. In parallel with the increase in overall myopia, there has been a rise in the prevalence of high myopia (≤−6 diopters [D]), which is associated with serious ocular complications such as posterior staphyloma, retinal degeneration, retinal detachment, and represents a leading cause of blindness worldwide. Furthermore, myopia is appearing with greater prevalence in young children, which places these children at greater risk of developing high myopia, with its associated complications. Despite continued research on the regulation of eye size and refraction, prior to the present work, no therapeutic targets have been identified and no pharmaceutical or optometric approaches have proven effective in the majority of cases. The increasing prevalence of myopia, earlier age of onset, and increasing prevalence of serious ocular complications associated with high myopia emphasize the need for the identification of pharmaceutical targets for the development of an effective therapy. The presently described novel compounds can be delivered to the eye either systemically, or by non-invasive local delivery, for example via eyedrops, or other methods as described elsewhere herein.

The presently disclosed novel compounds can also be used as a male contraceptive, by inhibiting spermatogenesis, as RALDH2-generated retinoic acid is necessary for spermatogenesis. In the past, the compound WIN 18,446 was tested in human males and was shown to be a potent, reversible inhibitor of spermatogenesis without affecting testosterone levels. However due to the compound's non-selectivity against ALDH enzymes, patients who consumed alcohol while taking WIN 18,446, had violent "disulfiram" reactions, including acute vomiting and shortness of breath due to inhibition of ALDH2, an enzyme necessary for complete alcohol detoxification in the body. Since the novel compounds of the present disclosure are selective inhibitors of the RALDHs, and do not inhibit ALDH2, the alcohol-related side effects that are associated with WIN 18,446 treatment will not occur. Additionally, the presently disclosed novel compounds also have applications for the control of certain cancers that are associated with ALDH1A1 (RALDH1) overexpression (such as but not limited to high grade ductal carcinoma, multiple myeloma, and acute myeloid leukemia).

The presently disclosed compounds can also be used in therapies for inhibiting fat formation, such as in therapies for the treatment of obesity and diabetes, as well as in the treatment of atherosclerosis, liposarcomas, lipomas and other fat-based tumor and cancers. As the principal action of the present compounds is the irreversible inhibition of the RALDH enzymes by binding the active sites of these enzymes (as long as the compounds are applied), the present prevent the oxidation of retinaldehyde to retinoic acid. The inhibition of this oxidation reaction increases the intracellular concentrations of retinaldehyde. Previous studies have shown that retinaldehyde suppresses both adipogenic gene expression and adipocyte lipid accumulation in animals at all developmental stages.

The presently disclosed compounds can also be used for the generation of adult stem cell populations. Research indicates that retinoic acid is one of the signals that causes differentiation of progenitor cell populations into a variety of mature cell types. Inhibition of retinoic acid synthesis through the application of the presently disclosed compounds can thus be used for the generation of multipotent and pluripotent adult stem cells in cell cultures, tissues and organs both in vitro and in vivo. For example, retinoic acid has been shown to induce neuronal differentiation of mouse embryonic stem cells (Zhang, J. et al., 2015; *PLoS One.* 10: e0132566), and promote differentiation of F9 embryonal carcinoma cells, into primitive, parietal, and visceral endodermal cells (Hogan, B. L. M. et al., (1981) *Nature.* 291: 235-237), and multipotent P19 embryonal carcinoma cells into neuronal and glial tissue in vitro (Jones-Villeneuve, E. V. et al., (1982) *Journal of Cell Biology*, 94: 253-262). The compounds of the present disclosure can be used to induce dedifferentiation or reprogramming, of such cells, and others, once they have been induced to differentiate by retinoic acid.

Research Applications

It is well-established that retinoic acid plays a major role in the development of many organ systems of many animal species. Additionally, evidence is accumulating that implicates retinoic acid in the postnatal growth and development of a variety of tissues and organs including the brain, eye, bone, testes, and adipose. Experimental approaches to investigate the role of retinoic acid during development and/or growth have typically utilized genetic approaches in which the synthesis of retinoic acid is inhibited through conditional knock down of one or more of the RALDH enzymes. These genetic approaches have limitations including, (1) variable penetrance of the transgene, (2) utility of a conditional system that does not interfere with development (e.g., in the "tet-off" system, the tetracycline transactivator (tTA) protein is toxic to a number of developing organisms), (3) off-target effects of transcription inducers (such as doxycycline, known to alter matrix metalloproteinase activity), and (4) the requirement for a model organism suitable for transgenic approaches (i.e., mice). Use of the presently disclosed compounds can serve as an alternative to these genetic approaches to inhibit retinoic acid synthesis in a variety of experimental settings, since they inhibit all three RALDH isoforms, and have no activity on other members of the ALDH superfamily (as noted above). Moreover, the pharmaceutical inhibition of RALDH with the present compounds is reversible following removal of the treatment, since RALDH protein expression is not inhibited by the compound, and no other confounding agents would be introduced into the system.

In certain embodiments, the RALDH inhibitors (i.e., active agents) of the present disclosure are compounds according the formula I (including all stereoisomers):

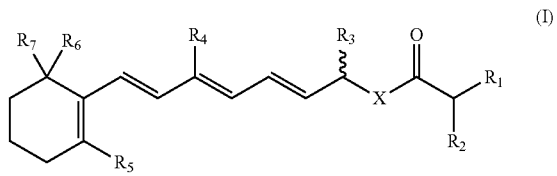

(I)

wherein
X is C, O or NH;
$R_1$ is H, F, Cl, Br, I, $NH_2$, OH, or $CH_3$;
$R_2$ is H, F, Cl, Br, I, $NH_2$, OH, or $CH_3$;
$R_3$ is H, $CH_3$, $CH_2CH_3$, $CH(CH_3)_2$, $C_6H_5$, or $CH_2(C_6H_5)$, with either a (R) or (S) configuration;
$R_4$ is $CH_3$, $CH_2CH_3$, $CH(CH_3)_2$, $C_6H_5$, or $CH_2(C_6H_5)$;
$R_5$ is $CH_3$, $CH_2CH_3$, $CH(CH_3)_2$, $C_6H_5$, or $CH_2(C_6H_5)$;
$R_6$ is $CH_3$, $CH_2CH_3$, $CH(CH_3)_2$, $C_6H_5$, or $CH_2(C_6H_5)$; and
$R_7$ is $CH_3$, $CH_2CH_3$, $CH(CH_3)_2$, $C_6H_5$, or $CH_2(C_6H_5)$.

In certain embodiments of formula I, at least one of $R_1$ and $R_2$ is not H, and/or at least one of $R_6$ and $R_7$ is $CH_3$.

In certain embodiments, the RALDH inhibitors of the present disclosure are compounds according the formula II:

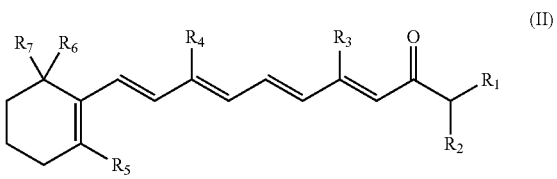

(II)

wherein
$R_1$ is H, F, Cl, Br, I, $NH_2$, OH, or $CH_3$;
$R_2$ is H, F, Cl, Br, I, $NH_2$, OH, or $CH_3$, with the proviso that at least one of $R_1$ and $R_2$ is not H;
$R_3$ is $CH_3$, $CH_2CH_3$, $CH(CH_3)_2$, $C_6H_5$, or $CH_2(C_6H_5)$;
$R_4$ is $CH_3$, $CH_2CH_3$, $CH(CH_3)_2$, $C_6H_5$, or $CH_2(C_6H_5)$;
$R_5$ is $CH_3$, $CH_2CH_3$, $CH(CH_3)_2$, $C_6H_5$, or $CH_2(C_6H_5)$;
$R_6$ is $CH_3$, $CH_2CH_3$, $CH(CH_3)_2$, $C_6H_5$, or $CH_2(C_6H_5)$; and
$R_7$ is $CH_3$, $CH_2CH_3$, $CH(CH_3)_2$, $C_6H_5$, or $CH_2(C_6H_5)$, with the proviso that at least one of $R_6$ and $R_7$ is $CH_3$.

In certain embodiments of the compound of formula I, wherein X is C: at least one of $R_1$ and $R_2$ is Cl; or at least one of $R_3$, $R_4$, and $R_5$ is $CH_3$; or at least one of $R_6$, and $R_7$ is $CH_3$; or at least one of $R_1$ and $R_2$ is Cl, and at least one of $R_3$, $R_4$, and $R_5$ is $CH_3$; or at least one of $R_1$ and $R_2$ is Cl, and at least one of $R_6$, and $R_7$ is $CH_3$; or at least one of $R_3$, $R_4$, and $R_5$ is $CH_3$, and at least one of $R_6$, and $R_7$ is $CH_3$; or at least one of $R_1$ and $R_2$ is Cl, and at least one of $R_3$, $R_4$, and $R_5$ is $CH_3$, and at least one of $R_6$, and $R_7$ is $CH_3$; or $R_1$ and $R_2$ are Cl, and $R_3$ and $R_4$ are $CH_3$; or $R_1$ and $R_2$ are Cl, and $R_6$ and $R_7$ are $CH_3$; or $R_3$ and $R_4$ are $CH_3$, and $R_6$ and $R_7$ are $CH_3$.

In certain embodiments of the compound of formula I, wherein X is O: at least one of $R_1$ and $R_2$ is Cl; or at least one of $R_3$, $R_4$, and $R_5$ is $CH_3$; or at least one of $R_6$, and $R_7$ is $CH_3$; or at least one of $R_1$ and $R_2$ is Cl, and at least one of $R_3$, $R_4$, and $R_5$ is $CH_3$; or at least one of $R_1$ and $R_2$ is Cl, and at least one of $R_6$, and $R_7$ is $CH_3$; or at least one of $R_3$, $R_4$, and $R_5$ is $CH_3$, and at least one of $R_6$, and $R_7$ is $CH_3$; or at least one of $R_1$ and $R_2$ is Cl, and at least one of $R_3$, $R_4$, and $R_5$ is $CH_3$, and at least one of $R_6$, and $R_7$ is $CH_3$; or $R_1$ and $R_2$ are Cl, and $R_3$ and $R_4$ are $CH_3$; or $R_1$ and $R_2$ are Cl, and $R_6$ and $R_7$ are $CH_3$; or $R_3$ and $R_4$ are $CH_3$, and $R_6$ and $R_7$ are $CH_3$.

In certain embodiments of the compound of formula I, wherein X is NH: at least one of $R_1$ and $R_2$ is Cl; or at least one of $R_3$, $R_4$, and $R_5$ is $CH_3$; or at least one of $R_6$, and $R_7$ is $CH_3$; or at least one of $R_1$ and $R_2$ is Cl, and at least one of $R_3$, $R_4$, and $R_5$ is $CH_3$; or at least one of $R_1$ and $R_2$ is Cl, and at least one of $R_6$, and $R_7$ is $CH_3$; or at least one of $R_3$, $R_4$, and $R_5$ is $CH_3$, and at least one of $R_6$, and $R_7$ is $CH_3$; or at least one of $R_1$ and $R_2$ is Cl, and at least one of $R_3$, $R_4$, and $R_5$ is $CH_3$, and at least one of $R_6$, and $R_7$ is $CH_3$; or $R_1$ and $R_2$ are Cl, and $R_3$ and $R_4$ are $CH_3$; or $R_1$ and $R_2$ are Cl, and $R_6$ and $R_7$ are $CH_3$; or $R_3$ and $R_4$ are $CH_3$, and $R_6$ and $R_7$ are $CH_3$.

In certain embodiments, the RALDH inhibitors of the present disclosure are compounds according the formula III, including all stereoisomers;

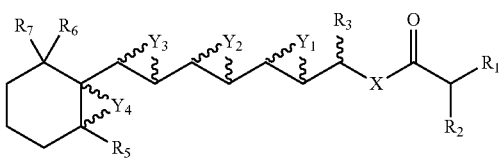

(III)

wherein
X is C, O or NH;
$R_1$ is H, F, Cl, Br, I, $NH_2$, OH, or $CH_3$;
$R_2$ is H, F, Cl, Br, I, $NH_2$, OH, or $CH_3$;
$R_3$ is $CH_3$, $CH_2CH_3$, $CH(CH_3)_2$, $C_6H_5$, or $CH_2(C_6H_5)$, with either a (R) or (S) configuration;
$R_5$ is $CH_3$, $CH_2CH_3$, $CH(CH_3)_2$, $C_6H_5$, or $CH_2(C_6H_5)$;
$R_6$ is $CH_3$, $CH_2CH_3$, $CH(CH_3)_2$, $C_6H_5$, or $CH_2(C_6H_5)$; and
$R_7$ is $CH_3$, $CH_2CH_3$, $CH(CH_3)_2$, $C_6H_5$, or $CH_2(C_6H_5)$;
$Y_1$ is a alkene (pi bond), $CH_2$, $CF_2$, $CBr_2$, $Cl_2$, O, S, NH, or $NCH_3$, with either a (R) or (S) configuration;
$Y_2$ is a alkene (pi bond), $CH_2$, $CF_2$, $CBr_2$, $Cl_2$, O, S, NH, or $NCH_3$, with either a (R) or (S) configuration;
$Y_3$ is a alkene (pi bond), $CH_2$, $CF_2$, $CBr_2$, $Cl_2$, O, S, NH, or $NCH_3$, with either a (R) or (S) configuration; and
$Y_4$ is a alkene (pi bond), $CH_2$, $CF_2$, $CBr_2$, $Cl_2$, O, S, NH, or $NCH_3$, with either a (R) or (S) configuration.

In certain embodiments of formula III, at least one of $R_1$ and $R_2$ is not H. In certain embodiments of formula III, at least one of $R_6$ and $R_7$ is $CH_3$. In certain embodiments when $Y_2$ is an alkene (pi bond), compounds having formula III could also include an $R_4$ group, as in formulas I and II, wherein $R_4$ is $CH_3$, $CH_2CH_3$, $CH(CH_3)_2$, $C_6H_5$, or $CH_2(C_6H_5)$.

In certain embodiments of formula III, at least one of $Y_1$, $Y_2$, $Y_3$, and $Y_4$ is not an alkene (pi bond). In such embodiments, the at least one of $Y_1$, $Y_2$, $Y_3$, and $Y_4$ forms a three-membered ring such as a cyclopropane, epoxide (oxirane), episulfide (thiirane), or aziridine, which enhances the stability of the compound.

In a non-limiting example, formula III has the formula IIIa below (including all stereoisomers) when $Y_1$ is an alkene (pi bond), $CH_2$, $CF_2$, $CBr_2$, $Cl_2$, O, S, NH, or $NCH_3$; $Y_2$, $Y_3$, and $Y_4$ are alkenes (pi bonds); and an $R_4$ ($CH_3$, $CH_2CH_3$, $CH(CH_3)_2$, $C_6H_5$, or $CH_2(C_6H_5)$) is linked to the carbon in the 8 position of the backbone of formula III (refer to structure 1 of Example 1 below):

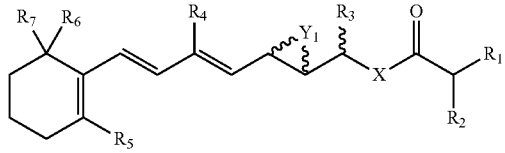
(IIIa)

In another non-limiting example, formula III has the formula IIIb below (including all stereoisomers) when $Y_3$ is an alkene (pi bond), $CH_2$, $CF_2$, $CBr_2$, $Cl_2$, O, S, NH, or $NCH_3$; $Y_1$, $Y_2$, and $Y_4$ are alkenes (pi bonds); and an $R_4$ ($CH_3$, $CH_2CH_3$, $CH(CH_3)_2$, $C_6H_5$, or $CH_2(C_6H_5)$) is linked to the carbon in the 8 position of the backbone of formula III:

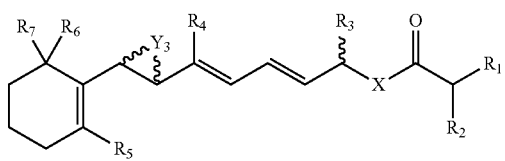
(IIIb)

In another non-limiting example, formula III has the formula IIIc below (including all stereoisomers) when $Y_2$ is an alkene (pi bond), $CH_2$, $CF_2$, $CBr_2$, $Cl_2$, O, S, NH, or $NCH_3$; and $Y_1$, $Y_3$, and $Y_4$ are alkenes (pi bonds):

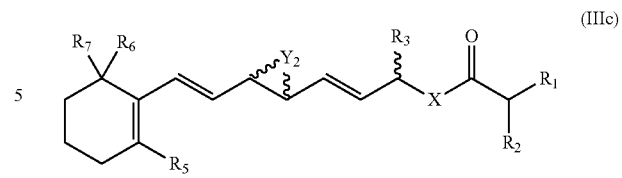
(IIIc)

In another non-limiting example, formula III has the formula IIId below (including all stereoisomers) when $Y_4$ is an alkene (pi bond), $CH_2$, $CF_2$, $CBr_2$, $Cl_2$, O, S, NH, or $NCH_3$; $Y_1$, $Y_2$, and $Y_3$ are alkenes (pi bonds); and an $R_4$ ($CH_3$, $CH_2CH_3$, $CH(CH_3)_2$, $C_6H_5$, or $CH_2(C_6H_5)$) is linked to the carbon in the 8 position of the backbone of formula III:

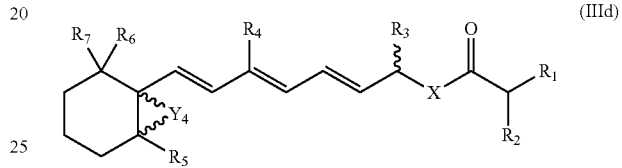
(IIId)

Particular but non-limiting examples of the compounds of the present disclosure include compounds according to formulas I, II, and III having specific $R_1$, $R_2$, $R_3$, $R_4$, $R_5$, $R_6$, and $R_7$ constituents in combinations as indicated in Table 1 (including all stereoisomers).

TABLE 1

Examples of compounds according to formulas I, II, and III. X of formulas I and III may be C, O, or NH.

|  | $R_1$ | $R_2$ | $R_3$ | $R_4$ | $R_5$ | $R_6$ | $R_7$ |
|---|---|---|---|---|---|---|---|
| Compound 1 | Cl | Cl | $CH_3$ | $CH_3$ | $CH_3$ | $CH_3$ | $CH_3$ |
| Compound 2 | Br | Br | $CH_3$ | $CH_3$ | $CH_3$ | $CH_3$ | $CH_3$ |
| Compound 3 | F | F | $CH_3$ | $CH_3$ | $CH_3$ | $CH_3$ | $CH_3$ |
| Compound 4 | H | Cl | $CH_3$ | $CH_3$ | $CH_3$ | $CH_3$ | $CH_3$ |
| Compound 5 | H | Br | $CH_3$ | $CH_3$ | $CH_3$ | $CH_3$ | $CH_3$ |
| Compound 6 | H | F | $CH_3$ | $CH_3$ | $CH_3$ | $CH_3$ | $CH_3$ |
| Compound 7 | Cl | Cl | $CH_2CH_3$ | $CH_3$ | $CH_3$ | $CH_3$ | $CH_3$ |
| Compound 8 | Cl | Cl | $CH(CH_3)_2$ | $CH_3$ | $CH_3$ | $CH_3$ | $CH_3$ |
| Compound 9 | Cl | Cl | $CH_3$ | $CH_2CH_3$ | $CH_3$ | $CH_3$ | $CH_3$ |
| Compound 10 | Cl | Cl | $CH_3$ | $CH(CH_3)_2$ | $CH_3$ | $CH_3$ | $CH_3$ |
| Compound 11 | Cl | Cl | $CH_3$ | $CH_3$ | $CH_2CH_3$ | $CH_3$ | $CH_3$ |
| Compound 12 | Cl | Cl | $CH_3$ | $CH_3$ | $CH(CH_3)_2$ | $CH_3$ | $CH_3$ |
| Compound 13 | H | Cl | $CH_3$ | $CH_3$ | $CH_3$ | $CH_2CH_3$ | $CH_3$ |
| Compound 14 | Cl | Cl | $CH_3$ | $CH_3$ | $CH_3$ | $CH(CH_3)_2$ | $CH_3$ |
| Compound 15 | Cl | Cl | $C_6H_5$ | $CH_3$ | $CH_3$ | $CH_3$ | $CH_3$ |
| Compound 16 | Cl | Cl | $CH_3$ | $C_6H_5$ | $CH_3$ | $CH_3$ | $CH_3$ |
| Compound 17 | Cl | Cl | $CH_3$ | $CH_3$ | $C_6H_5$ | $CH_3$ | $CH_3$ |
| Compound 18 | Cl | H | $CH_3$ | $CH_3$ | $CH_3$ | $C_6H_5$ | $CH_3$ |
| Compound 19 | Cl | Cl | $CH_2(C_6H_5)$ | $CH_3$ | $CH_3$ | $CH_3$ | $CH_3$ |
| Compound 20 | Cl | Cl | $CH_3$ | $CH_2(C_6H_5)$ | $CH_3$ | $CH_3$ | $CH_3$ |
| Compound 21 | Cl | Cl | $CH_3$ | $CH_3$ | $CH_2(C_6H_5)$ | $CH_3$ | $CH_3$ |
| Compound 22 | Cl | Cl | $CH_3$ | $CH_3$ | $CH_3$ | $CH_2(C_6H_5)$ | $CH_3$ |
| Compound 23 | Br | Br | $CH_2CH_3$ | $CH_3$ | $CH_3$ | $CH_3$ | $CH_3$ |
| Compound 24 | Br | Br | $CH(CH_3)_2$ | $CH_3$ | $CH_3$ | $CH_3$ | $CH_3$ |
| Compound 25 | Br | Br | $CH_3$ | $CH_2CH_3$ | $CH_3$ | $CH_3$ | $CH_3$ |
| Compound 26 | Br | Br | $CH_3$ | $CH(CH_3)_2$ | $CH_3$ | $CH_3$ | $CH_3$ |
| Compound 27 | Br | Br | $CH_3$ | $CH_3$ | $CH_2CH_3$ | $CH_3$ | $CH_3$ |
| Compound 28 | Br | H | $CH_3$ | $CH_3$ | $CH(CH_3)_2$ | $CH_3$ | $CH_3$ |
| Compound 29 | Br | Br | $CH_3$ | $CH_3$ | $CH_3$ | $CH_2CH_3$ | $CH_3$ |
| Compound 30 | Br | Br | $CH_3$ | $CH_3$ | $CH_3$ | $CH(CH_3)_2$ | $CH_3$ |
| Compound 31 | Br | Br | $C_6H_5$ | $CH_3$ | $CH_3$ | $CH_3$ | $CH_3$ |
| Compound 32 | Br | Br | $CH_3$ | $C_6H_5$ | $CH_3$ | $CH_3$ | $CH_3$ |
| Compound 33 | Br | Br | $CH_3$ | $CH_3$ | $C_6H_5$ | $CH_3$ | $CH_3$ |
| Compound 34 | H | Br | $CH_3$ | $CH_3$ | $CH_3$ | $C_6H_5$ | $CH_3$ |

TABLE 1-continued

Examples of compounds according to formulas I, II, and III. X of formulas I and III may be C, O, or NH.

| | $R_1$ | $R_2$ | $R_3$ | $R_4$ | $R_5$ | $R_6$ | $R_7$ |
|---|---|---|---|---|---|---|---|
| Compound 35 | Br | Br | $CH_2(C_6H_5)$ | $CH_3$ | $CH_3$ | $CH_3$ | $CH_3$ |
| Compound 36 | Br | Br | $CH_3$ | $CH_2(C_6H_5)$ | $CH_3$ | $CH_3$ | $CH_3$ |
| Compound 37 | Br | Br | $CH_3$ | $CH_3$ | $CH_2(C_6H_5)$ | $CH_3$ | $CH_3$ |
| Compound 38 | Br | Br | $CH_3$ | $CH_3$ | $CH_3$ | $CH_2(C_6H_5)$ | $CH_3$ |
| Compound 39 | F | F | $CH_2CH_3$ | $CH_3$ | $CH_3$ | $CH_3$ | $CH_3$ |
| Compound 40 | F | F | $CH(CH_3)_2$ | $CH_3$ | $CH_3$ | $CH_3$ | $CH_3$ |
| Compound 41 | F | F | $CH_3$ | $CH_2CH_3$ | $CH_3$ | $CH_3$ | $CH_3$ |
| Compound 42 | F | F | $CH_3$ | $CH(CH_3)_2$ | $CH_3$ | $CH_3$ | $CH_3$ |
| Compound 43 | F | F | $CH_3$ | $CH_3$ | $CH_2CH_3$ | $CH_3$ | $CH_3$ |
| Compound 44 | F | F | $CH_3$ | $CH_3$ | $CH(CH_3)_2$ | $CH_3$ | $CH_3$ |
| Compound 45 | H | F | $CH_3$ | $CH_3$ | $CH_3$ | $CH_2CH_3$ | $CH_3$ |
| Compound 46 | F | F | $CH_3$ | $CH_3$ | $CH_3$ | $CH(CH_3)_2$ | $CH_3$ |
| Compound 47 | F | F | $C_6H_5$ | $CH_3$ | $CH_3$ | $CH_3$ | $CH_3$ |
| Compound 48 | F | F | $CH_3$ | $C_6H_5$ | $CH_3$ | $CH_3$ | $CH_3$ |
| Compound 49 | F | H | $CH_3$ | $CH_3$ | $C_6H_5$ | $CH_3$ | $CH_3$ |
| Compound 50 | F | F | $CH_3$ | $CH_3$ | $CH_3$ | $C_6H_5$ | $CH_3$ |
| Compound 51 | F | F | $CH_2(C_6H_5)$ | $CH_3$ | $CH_3$ | $CH_3$ | $CH_3$ |
| Compound 52 | F | F | $CH_3$ | $CH_2(C_6H_5)$ | $CH_3$ | $CH_3$ | $CH_3$ |
| Compound 53 | F | F | $CH_3$ | $CH_3$ | $CH_2(C_6H_5)$ | $CH_3$ | $CH_3$ |
| Compound 54 | F | F | $CH_3$ | $CH_3$ | $CH_3$ | $CH_2(C_6H_5)$ | $CH_3$ |
| Compound 55 | $NH_2$ | H | $CH_3$ | $CH_3$ | $CH_3$ | $CH_3$ | $CH_3$ |
| Compound 56 | $NH_2$ | H | $CH_2CH_3$ | $CH_3$ | $CH_3$ | $CH_3$ | $CH_3$ |
| Compound 57 | $NH_2$ | H | $CH(CH_3)_2$ | $CH_3$ | $CH_3$ | $CH_3$ | $CH_3$ |
| Compound 58 | $NH_2$ | H | $CH_3$ | $CH_2CH_3$ | $CH_3$ | $CH_3$ | $CH_3$ |
| Compound 59 | $NH_2$ | H | $CH_3$ | $CH(CH_3)_2$ | $CH_3$ | $CH_3$ | $CH_3$ |
| Compound 60 | $NH_2$ | H | $CH_3$ | $CH_3$ | $CH_2CH_3$ | $CH_3$ | $CH_3$ |
| Compound 61 | $NH_2$ | H | $CH_3$ | $CH_3$ | $CH(CH_3)_2$ | $CH_3$ | $CH_3$ |
| Compound 62 | $NH_2$ | H | $CH_3$ | $CH_3$ | $CH_3$ | $CH_2CH_3$ | $CH_3$ |
| Compound 63 | $NH_2$ | H | $CH_3$ | $CH_3$ | $CH_3$ | $CH(CH_3)_2$ | $CH_3$ |
| Compound 64 | $NH_2$ | H | $C_6H_5$ | $CH_3$ | $CH_3$ | $CH_3$ | $CH_3$ |
| Compound 65 | $NH_2$ | H | $CH_3$ | $C_6H_5$ | $CH_3$ | $CH_3$ | $CH_3$ |
| Compound 66 | $NH_2$ | H | $CH_3$ | $CH_3$ | $C_6H_5$ | $CH_3$ | $CH_3$ |
| Compound 67 | $NH_2$ | H | $CH_3$ | $CH_3$ | $CH_3$ | $C_6H_5$ | $CH_3$ |
| Compound 68 | $NH_2$ | H | $CH_2(C_6H_5)$ | $CH_3$ | $CH_3$ | $CH_3$ | $CH_3$ |
| Compound 69 | $NH_2$ | H | $CH_3$ | $CH_2(C_6H_5)$ | $CH_3$ | $CH_3$ | $CH_3$ |
| Compound 70 | $NH_2$ | H | $CH_3$ | $CH_3$ | $CH_2(C_6H_5)$ | $CH_3$ | $CH_3$ |
| Compound 71 | $NH_2$ | H | $CH_3$ | $CH_3$ | $CH_3$ | $CH_2(C_6H_5)$ | $CH_3$ |
| Compound 72 | $NH_2$ | $NH_2$ | $CH_3$ | $CH_3$ | $CH_3$ | $CH_3$ | $CH_3$ |
| Compound 73 | $NH_2$ | $NH_2$ | $CH_2CH_3$ | $CH_3$ | $CH_3$ | $CH_3$ | $CH_3$ |
| Compound 74 | $NH_2$ | $NH_2$ | $CH(CH_3)_2$ | $CH_3$ | $CH_3$ | $CH_3$ | $CH_3$ |
| Compound 75 | $NH_2$ | $NH_2$ | $CH_3$ | $CH_2CH_3$ | $CH_3$ | $CH_3$ | $CH_3$ |
| Compound 76 | $NH_2$ | $NH_2$ | $CH_3$ | $CH(CH_3)_2$ | $CH_3$ | $CH_3$ | $CH_3$ |
| Compound 77 | $NH_2$ | $NH_2$ | $CH_3$ | $CH_3$ | $CH_2CH_3$ | $CH_3$ | $CH_3$ |
| Compound 78 | $NH_2$ | $NH_2$ | $CH_3$ | $CH_3$ | $CH(CH_3)_2$ | $CH_3$ | $CH_3$ |
| Compound 79 | $NH_2$ | $NH_2$ | $CH_3$ | $CH_3$ | $CH_3$ | $CH_2CH_3$ | $CH_3$ |
| Compound 80 | $NH_2$ | $NH_2$ | $CH_3$ | $CH_3$ | $CH_3$ | $CH(CH_3)_2$ | $CH_3$ |
| Compound 81 | $NH_2$ | H | $C_6H_5$ | $CH_3$ | $CH_3$ | $CH_3$ | $CH_3$ |
| Compound 82 | $NH_2$ | $NH_2$ | $CH_3$ | $C_6H_5$ | $CH_3$ | $CH_3$ | $CH_3$ |
| Compound 83 | $NH_2$ | $NH_2$ | $CH_3$ | $CH_3$ | $C_6H_5$ | $CH_3$ | $CH_3$ |
| Compound 84 | $NH_2$ | $NH_2$ | $CH_3$ | $CH_3$ | $CH_3$ | $C_6H_5$ | $CH_3$ |
| Compound 85 | $NH_2$ | $NH_2$ | $CH_2(C_6H_5)$ | $CH_3$ | $CH_3$ | $CH_3$ | $CH_3$ |
| Compound 86 | $NH_2$ | $NH_2$ | $CH_3$ | $CH_2(C_6H_5)$ | $CH_3$ | $CH_3$ | $CH_3$ |
| Compound 87 | $NH_2$ | $NH_2$ | $CH_3$ | $CH_3$ | $CH_2(C_6H_5)$ | $CH_3$ | $CH_3$ |
| Compound 88 | $NH_2$ | $NH_2$ | $CH_3$ | $CH_3$ | $CH_3$ | $CH_2(C_6H_5)$ | $CH_3$ |
| Compound 89 | OH | H | $CH_3$ | $CH_3$ | $CH_3$ | $CH_3$ | $CH_3$ |
| Compound 90 | OH | H | $CH_2CH_3$ | $CH_3$ | $CH_3$ | $CH_3$ | $CH_3$ |
| Compound 91 | OH | H | $CH(CH_3)_2$ | $CH_3$ | $CH_3$ | $CH_3$ | $CH_3$ |
| Compound 92 | OH | H | $CH_3$ | $CH_2CH_3$ | $CH_3$ | $CH_3$ | $CH_3$ |
| Compound 93 | OH | H | $CH_3$ | $CH(CH_3)_2$ | $CH_3$ | $CH_3$ | $CH_3$ |
| Compound 94 | OH | H | $CH_3$ | $CH_3$ | $CH_2CH_3$ | $CH_3$ | $CH_3$ |
| Compound 95 | OH | H | $CH_3$ | $CH_3$ | $CH(CH_3)_2$ | $CH_3$ | $CH_3$ |
| Compound 96 | OH | H | $CH_3$ | $CH_3$ | $CH_3$ | $CH_2CH_3$ | $CH_3$ |
| Compound 97 | OH | H | $CH_3$ | $CH_3$ | $CH_3$ | $CH(CH_3)_2$ | $CH_3$ |
| Compound 98 | OH | H | $C_6H_5$ | $CH_3$ | $CH_3$ | $CH_3$ | $CH_3$ |
| Compound 99 | OH | H | $CH_3$ | $C_6H_5$ | $CH_3$ | $CH_3$ | $CH_3$ |
| Compound 100 | OH | H | $CH_3$ | $CH_3$ | $C_6H_5$ | $CH_3$ | $CH_3$ |
| Compound 101 | OH | H | $CH_3$ | $CH_3$ | $CH_3$ | $C_6H_5$ | $CH_3$ |
| Compound 102 | OH | H | $CH_2(C_6H_5)$ | $CH_3$ | $CH_3$ | $CH_3$ | $CH_3$ |
| Compound 103 | OH | H | $CH_3$ | $CH_2(C_6H_5)$ | $CH_3$ | $CH_3$ | $CH_3$ |
| Compound 104 | OH | H | $CH_3$ | $CH_3$ | $CH_2(C_6H_5)$ | $CH_3$ | $CH_3$ |
| Compound 105 | OH | H | $CH_3$ | $CH_3$ | $CH_3$ | $CH_2(C_6H_5)$ | $CH_3$ |
| Compound 106 | OH | OH | $CH_3$ | $CH_3$ | $CH_3$ | $CH_3$ | $CH_3$ |
| Compound 107 | OH | OH | $CH_2CH_3$ | $CH_3$ | $CH_3$ | $CH_3$ | $CH_3$ |
| Compound 108 | OH | OH | $CH(CH_3)_2$ | $CH_3$ | $CH_3$ | $CH_3$ | $CH_3$ |
| Compound 109 | OH | OH | $CH_3$ | $CH_2CH_3$ | $CH_3$ | $CH_3$ | $CH_3$ |

TABLE 1-continued

Examples of compounds according to formulas I, II, and III. X of formulas I and III may be C, O, or NH.

| | $R_1$ | $R_2$ | $R_3$ | $R_4$ | $R_5$ | $R_6$ | $R_7$ |
|---|---|---|---|---|---|---|---|
| Compound 110 | OH | OH | $CH_3$ | $CH(CH_3)_2$ | $CH_3$ | $CH_3$ | $CH_3$ |
| Compound 111 | OH | OH | $CH_3$ | $CH_3$ | $CH_2CH_3$ | $CH_3$ | $CH_3$ |
| Compound 112 | OH | OH | $CH_3$ | $CH_3$ | $CH(CH_3)_2$ | $CH_3$ | $CH_3$ |
| Compound 113 | OH | OH | $CH_3$ | $CH_3$ | $CH_3$ | $CH_2CH_3$ | $CH_3$ |
| Compound 114 | OH | OH | $CH_3$ | $CH_3$ | $CH_3$ | $CH(CH_3)_2$ | $CH_3$ |
| Compound 115 | OH | OH | $C_6H_5$ | $CH_3$ | $CH_3$ | $CH_3$ | $CH_3$ |
| Compound 116 | OH | OH | $CH_3$ | $C_6H_5$ | $CH_3$ | $CH_3$ | $CH_3$ |
| Compound 117 | OH | OH | $CH_3$ | $CH_3$ | CgHs | $CH_3$ | $CH_3$ |
| Compound 118 | OH | OH | $CH_3$ | $CH_3$ | $CH_3$ | CsHs | $CH_3$ |
| Compound 119 | OH | OH | $CH_2(C_6H_5)$ | $CH_3$ | $CH_3$ | $CH_3$ | $CH_3$ |
| Compound 120 | OH | OH | $CH_3$ | $CH_2(C_6H_5)$ | $CH_3$ | $CH_3$ | $CH_3$ |
| Compound 121 | OH | OH | $CH_3$ | $CH_3$ | $CH_2(C_6H_5)$ | $CH_3$ | $CH_3$ |
| Compound 122 | OH | OH | $CH_3$ | $CH_3$ | $CH_3$ | $CH_2(C_6H_5)$ | $CH_3$ |
| Compound 123 | $CH_3$ | H | $CH_3$ | $CH_3$ | $CH_3$ | $CH_3$ | $CH_3$ |
| Compound 124 | $CH_3$ | H | $CH_2CH_3$ | $CH_3$ | $CH_3$ | $CH_3$ | $CH_3$ |
| Compound 125 | $CH_3$ | H | $CH(CH_3)_2$ | $CH_3$ | $CH_3$ | $CH_3$ | $CH_3$ |
| Compound 126 | $CH_3$ | H | $CH_3$ | $CH_2CH_3$ | $CH_3$ | $CH_3$ | $CH_3$ |
| Compound 127 | $CH_3$ | H | $CH_3$ | $CH(CH_3)_2$ | $CH_3$ | $CH_3$ | $CH_3$ |
| Compound 128 | $CH_3$ | H | $CH_3$ | $CH_3$ | $CH_2CH_3$ | $CH_3$ | $CH_3$ |
| Compound 129 | $CH_3$ | H | $CH_3$ | $CH_3$ | $CH(CH_3)_2$ | $CH_3$ | $CH_3$ |
| Compound 130 | $CH_3$ | H | $CH_3$ | $CH_3$ | $CH_3$ | $CH_2CH_3$ | $CH_3$ |
| Compound 131 | $CH_3$ | H | $CH_3$ | $CH_3$ | $CH_3$ | $CH(CH_3)_2$ | $CH_3$ |
| Compound 132 | $CH_3$ | H | $C_6H_5$ | $CH_3$ | $CH_3$ | $CH_3$ | $CH_3$ |
| Compound 133 | $CH_3$ | H | $CH_3$ | $C_6H_5$ | $CH_3$ | $CH_3$ | $CH_3$ |
| Compound 134 | $CH_3$ | H | $CH_3$ | $CH_3$ | $C_6H_5$ | $CH_3$ | $CH_3$ |
| Compound 135 | $CH_3$ | H | $CH_3$ | $CH_3$ | $CH_3$ | $C_6H_5$ | $CH_3$ |
| Compound 136 | $CH_3$ | H | $CH_2(C_6H_5)$ | $CH_3$ | $CH_3$ | $CH_3$ | $CH_3$ |
| Compound 137 | $CH_3$ | H | $CH_3$ | $CH_2(C_6H_5)$ | $CH_3$ | $CH_3$ | $CH_3$ |
| Compound 138 | $CH_3$ | H | $CH_3$ | $CH_3$ | $CH_2(C_6H_5)$ | $CH_3$ | $CH_3$ |
| Compound 139 | $CH_3$ | H | $CH_3$ | $CH_3$ | $CH_3$ | $CH_2(C_6H_5)$ | $CH_3$ |
| Compound 140 | $CH_3$ | $CH_3$ | $CH_3$ | $CH_3$ | $CH_3$ | $CH_3$ | $CH_3$ |
| Compound 141 | $CH_3$ | $CH_3$ | $CH_2CH_3$ | $CH_3$ | $CH_3$ | $CH_3$ | $CH_3$ |
| Compound 142 | $CH_3$ | $CH_3$ | $CH(CH_3)_2$ | $CH_3$ | $CH_3$ | $CH_3$ | $CH_3$ |
| Compound 143 | $CH_3$ | $CH_3$ | $CH_3$ | $CH_2CH_3$ | $CH_3$ | $CH_3$ | $CH_3$ |
| Compound 144 | $CH_3$ | $CH_3$ | $CH_3$ | $CH(CH_3)_2$ | $CH_3$ | $CH_3$ | $CH_3$ |
| Compound 145 | $CH_3$ | $CH_3$ | $CH_3$ | $CH_3$ | $CH_2CH_3$ | $CH_3$ | $CH_3$ |
| Compound 146 | $CH_3$ | $CH_3$ | $CH_3$ | $CH_3$ | $CH(CH_3)_2$ | $CH_3$ | $CH_3$ |
| Compound 147 | $CH_3$ | $CH_3$ | $CH_3$ | $CH_3$ | $CH_3$ | $CH_2CH_3$ | $CH_3$ |
| Compound 148 | $CH_3$ | $CH_3$ | $CH_3$ | $CH_3$ | $CH_3$ | $CH(CH_3)_2$ | $CH_3$ |
| Compound 149 | $CH_3$ | $CH_3$ | $C_6H_5$ | $CH_3$ | $CH_3$ | $CH_3$ | $CH_3$ |
| Compound 150 | $CH_3$ | $CH_3$ | $CH_3$ | $C_6H_5$ | $CH_3$ | $CH_3$ | $CH_3$ |
| Compound 151 | $CH_3$ | $CH_3$ | $CH_3$ | $CH_3$ | $C_6H_5$ | $CH_3$ | $CH_3$ |
| Compound 152 | $CH_3$ | $CH_3$ | $CH_3$ | $CH_3$ | $CH_3$ | $C_6H_5$ | $CH_3$ |
| Compound 153 | $CH_3$ | $CH_3$ | $CH_2(C_6H_5)$ | $CH_3$ | $CH_3$ | $CH_3$ | $CH_3$ |
| Compound 154 | $CH_3$ | $CH_3$ | $CH_3$ | $CH_2(C_6H_5)$ | $CH_3$ | $CH_3$ | $CH_3$ |
| Compound 155 | $CH_3$ | $CH_3$ | $CH_3$ | $CH_3$ | $CH_2(C_6H_5)$ | $CH_3$ | $CH_3$ |
| Compound 156 | $CH_3$ | $CH_3$ | $CH_3$ | $CH_3$ | $CH_3$ | $CH_2(C_6H_5)$ | $CH_3$ |

In certain embodiments, the RALDH inhibitors of the present disclosure are compounds according the formula IV (including all stereoisomers):

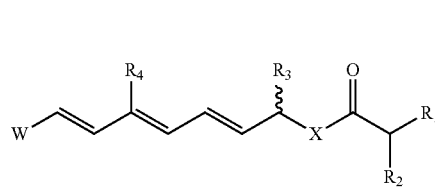

(IV)

wherein $R_1$ is H, F, Cl, Br, I, $NH_2$, OH, or $CH_3$;

$R_2$ is H, F, Cl, Br, I, $NH_2$, OH, or $CH_3$;

$R_3$ is $CH_3$, $CH_2CH_3$, $CH(CH_3)_2$, $C_6H_5$, or $CH_2(C_6H_5)$, with either a (R) or (S) configuration;

$R_4$ is $CH_3$, $CH_2CH_3$, $CH(CH_3)_2$, $C_6H_5$, or $CH_2(C_6H_5)$; and

W is a substituted heterocycle.

In at least certain embodiments of formula IV, at least one of $R_1$ and $R_2$ is not H.

In certain embodiments, the substituted heterocycle W is selected from the group consisting of a pyrimidine (e.g., $W_1$), indole (e.g., $W_2$), tetrahydropyridine (e.g., $W_3$), piperazine (e.g., $W_4$), pyrrolopyridine (e.g., $W_5$), pyrrolopyrimidine (e.g., $W_6$), pyrrolopyrazine (e.g., $W_7$), pyrazolopyrimidine (e.g., $W_8$), quinoline (e.g., $W_9$), and isoquinoline (e.g., $W_{10}$), wherein $R_5$ is H, F, $CH_3$, $CF_3$, OH, $OCH_3$, $NH_2$, $N(CH_3)_2$, $C_6H$, $CH_2(C_6H_5)$;

$R_9$ is H, F, $CH_3$, $CF_3$, OH, $OCH_3$, $NH_2$, $N(CH_3)_2$, $C_6H$, $CH_2(C_6H_5)$;

$R_{10}$ is H, F, $CH_3$, $CF_3$, OH, $OCH_3$, $NH_2$, $N(CH_3)_2$, $C_6H$, $CH_2(C_6H_5)$;

$R_{11}$ is H, F, $CH_3$, $CF_3$, OH, $OCH_3$, $NH_2$, $N(CH_3)_2$, $C_6H$, $CH_2(C_6H_5)$;

$R_{12}$ is H, F, $CH_3$, $CF_3$, OH, $OCH_3$, $NH_2$, $N(CH_3)_2$, $C_6H$, $CH_2(C_6H_5)$;

$R_{13}$ is H, F, $CH_3$, $CF_3$, OH, $OCH_3$, $NH_2$, $N(CH_3)_2$, $C_6H$, $CH_2(C_6H_5)$;

$R_{14}$ is H, F, $CH_3$, $CF_3$, OH, $OCH_3$, $NH_2$, $N(CH_3)_2$, $C_6H$, $CH_2(C_6H_5)$; and $R_{15}$ is H, F, $CH_3$, $CF_3$, OH, $OCH_3$, $NH_2$, $N(CH_3)_2$, $C_6H$, $CH_2(C_6H_5)$.

As noted, examples of substituted heterocycles which may comprise W include, but are not limited to, those represented by the following formulas $W_1$-$W_{10}$.

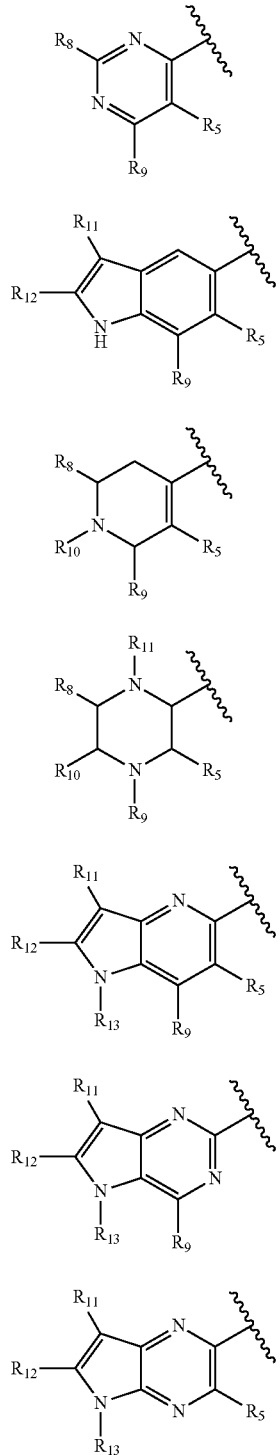

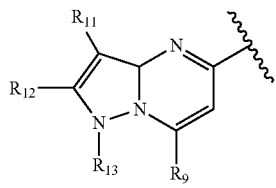

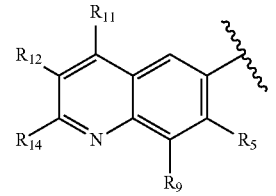

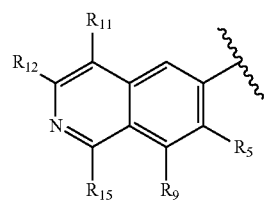

The following is an example of a compound which represents one embodiment of the present disclosure and is not intended to be limiting of the present disclosure.

Example 1

Synthesis of (3E,5E,7E,9E)-1,1-dichloro-4,8-dimethyl-10-(2,6,6-trimethylcyclohex-1-en-1-yl) deca-3,5,7,9-tetraen-2-one This example describes the synthesis and characterization of the non-limiting embodiment of a compound of the present disclosure having structure 1, wherein in formula II, $R_1$ and $R_2$ are Cl, and $R_3$, $R_4$, $R_5$, $R_6$, and $R_7$ are $CH_3$.

Structure 1:

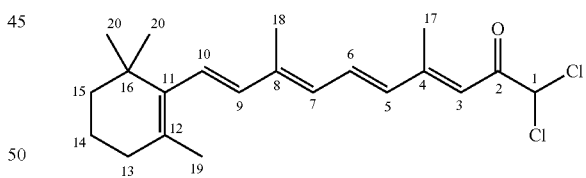

(3E,5E,7E,9E)-1,1-dichloro-4,8-dimethyl-10-(2,6,6-trimethylcyclohex-1-en-1-yl)deca-3,5,7,9-tetraen-2-one Methods Ethyl retinoate (40.1 mg, 0.122 mmol) was dissolved in dry ethyl ether (500 μL) under nitrogen. Dichloromethane (11.04, 0.171 mmol) was added via syringe. The dark yellow solution was cooled down to −78° C. LDA solution (2.0M in THF, 984, 0.195 mmol) was added dropwise over 3 minutes. Upon the addition of LDA, the color of the reaction mixture turned dark brown. The reaction mixture was stirred at −78° C. for additional 5 minutes. To the reaction mixture was then added 6N HCl (250 μL). The mixture was warmed to room temperature, diluted with ethyl ether (20 mL), washed with 1N HCl (30 mL×2) and with DI water (30 mL). The combined aqueous phase was back extracted with ethyl ether (20 mL×2). The combined organic phase was washed with brine (30 mL) and dried with $Na_2SO_4$. The solvent was removed under reduced pressure to afford crude product as a dark brown oil (40 mg). The reaction produced multiple products. The crude mixture was then separated via pTLC (4 plates) eluted with 4.5% EtOAc/hexane to afford five fractions: fraction 1 (Rf=0.63, 0.1 mg); fraction 2 (Rf=0.57, 3.6 mg); fraction 3 (Rf=0.48, 3.0 mg); fraction 4 (Rf=0.40, 0.1 mg); fraction 5 (Rf=0.31, 5.2 mg). The desired product was further purified from fraction 2 by HPLC using a Phenomenex C18 Luna semiprep column, 96-98% MeCN/water with 0.1% formic acid gradient in 9 minutes. This resulted in the pure desired product (yellow oil, 2.1 mg, 4.7% yield) with retention time at 16.7 minute.

All reactions were performed in oven-dried glassware under a positive pressure of nitrogen unless noted otherwise. Flask column chromatography was performed as described by Still et al. (Still, W. C., Kahn, M.; Mitra, A. *J. Org. Chem.* 1978, 43, 2923-2925) employing E. Merck silica gel 60 (230-400 mesh ASTM). Diethyl ether was passed through a solvent purification system utilizing alumina columns. Methylene chloride ($CH_2Cl_2$) was prepared by distillation with CaH2. TLC analyses and preparative TLC (pTLC) purification was performed on 250 μm Silica Gel 60 F254 plates purchased from EM Science and Fluka Analytical.

Instrumentation: Infrared spectra were recorded on an Shimadzu IRAffinity-1 instrument. $^1$H and $^{13}$CNMR spectra were recorded on a VNMRS 500 MHz-NMR Spectrometer. Chemical shifts for proton and carbon resonances are reported in ppm (δ) relative to the residual proton or the specified carbon in chloroform (δ 7.27, proton; 77.23, carbon). HPLC purification was performed on Shimadzu LCMS 2020. Semi-preparative HPLC was performed using a photodiode array detector with indicated columns and solvent conditions.

TLC Rf: desired compound 0.65 in 10% EtOAc/hex.

NMR analysis:
$^1$H NMR (500 MHz, $CDCl_3$) δ 7.21 (dd, J=15.0, 11.5 Hz, 1H), 6.49 (s, 1H), 6.39 (dd, J=18.0, 15.1 Hz, 2H), 6.24-6.15 (m, 2H), 5.84 (s, 1H), 2.44 (s, 3H), 2.05 (s, 3H), 2.04 (m, 2H), 1.68-1.59 (m, 2H), 1.52-1.46 (m, 2H), 1.05 (s, 6H) $^{13}$C NMR (126 MHz, $CDCl_3$) δ 186.46, 159.02, 141.93, 137.63, 137.05, 134.81, 134.38, 130.63, 130.03, 129.40, 118.02, 71.02, 39.60, 34.28, 33.17, 28.97, 21.77, 19.18, 14.96, 13.05

TABLE II

IR (film) analysis: 3440, 2920, 1680, 1558, 1440, 1360, 1150, 1080, 965, 785 $cm^{-1}$

| ID | δ($^1$H) | δ($^{13}$C) | Hs | Type | J (Hz) | COSY | HMBC |
|---|---|---|---|---|---|---|---|
| 1 | 5.84 | 71.02 | 1 | s | — | — | — |
| 2 | — | 186.46 | — | — | — | — | — |
| 3 | 6.49 | 118.02 | 1 | s | — | 2.43, 6.42 | 134.81, 186.46 |
| 4 | — | 159.02 | — | — | — | — | — |
| 5 | 6.42 | 134.81 | 1 | d | 15.00 | 7.24, 6.49 | 14.96, 118.02, 129.40 |
| 6 | 7.21 | 134.38 | 1 | dd | 11.5, 15.0 | 6.20, 6.42 | 159.02, 141.93 |
| 7 | 6.37 | 130.03 | 1 | d | 18.00 | 7.21, 6.17 | 14.96, 118.02 |
| 8 | — | 141.93 | — | — | — | — | — |
| 9 | 6.20 | 129.40 | 1 | d | 11.30 | 6.39 | 137.05 |
| 10 | 6.17 | 137.05 | 1 | d | 15.90 | — | 129.40, 137.63, 141.93 |
| 11 | — | 137.63 | — | — | — | — | — |
| 12 | — | 130.63 | — | — | — | — | — |
| 13 | 2.04 | 33.17 | 2 | m | — | 1.63 | 39.60, 137.05, 141.93 |
| 14 | 1.63 | 19.18 | 2 | m | — | 1.49, 2.03 | 34.28, 130.63 |
| 15 | 1.49 | 39.60 | 2 | m | — | 1.63 | 28.97, 34.28 |
| 16 | — | 34.28 | — | — | — | — | — |
| 17 | 2.44 | 14.96 | 3 | s | — | 6.49 | 118.02, 134.81, 159.02 |
| 18 | 2.05 | 13.05 | 3 | s | — | — | 118.02, 134.81, 159.02 |
| 19 | 1.74 | 21.77 | 3 | s | — | 2.05 | 33.17, 130.63, 137.63 |
| 20 | 1.05 | 28.97 | 6 | s | — | — | 28.97, 34.28, 39.60, 137.63 |

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. A compound according to formula I:

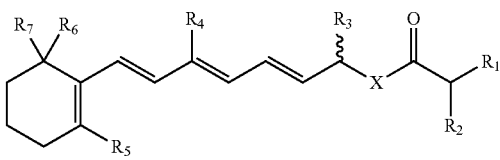

wherein
X is C, O or NH;
$R_1$ is Cl, F, Br, I, H, $NH_2$, OH, or $CH_3$;
$R_2$ is Cl, F, Br, I, H, $NH_2$, OH, or $CH_3$, with the proviso that at least one of $R_1$ and $R_2$ is not H;
$R_3$ is $CH_3$, H, $CH_2CH_3$, $CH(CH_3)_2$, $C_6H_5$, or $CH_2(C_6H_5)$, with either a (R) or (S) configuration;
$R_4$ is $CH_3$, $CH_2CH_3$, $CH(CH_3)_2$, $C_6H_5$, or $CH_2(C_6H_5)$;
$R_5$ is $CH_3$, $CH_2CH_3$, $CH(CH_3)_2$, $C_6H_5$, or $CH_2(C_6H_5)$;
$R_6$ is $CH_3$, $CH_2CH_3$, $CH(CH_3)_2$, $C_6H_5$, or $CH_2(C_6H_5)$; and
$R_7$ is $CH_3$, $CH_2CH_3$, $CH(CH_3)_2$, $C_6H_5$, or $CH_2(C_6H_5)$, with the proviso that at least one of $R_6$ and $R_7$ is $CH_3$.

2. The compound of claim 1, wherein X is C.

3. The compound of claim 1, wherein at least one of $R_1$ and $R_2$ is Cl.

4. The compound of claim 1, wherein at least one of $R_3$, $R_4$, and $R_5$ is $CH_3$.

5. The compound of claim 1, wherein at least one of $R_6$, and $R_7$ is $CH_3$.

6. The compound of claim 1, wherein at least one of $R_1$ and $R_2$ is Cl, and at least one of $R_3$, $R_4$, and $R_5$ is $CH_3$.

7. The compound of claim 1, wherein at least one of $R_1$ and $R_2$ is Cl, and at least one of $R_6$, and $R_7$ is $CH_3$.

8. The compound of claim 1, wherein at least one of $R_3$, $R_4$, and $R_5$ is $CH_3$, and at least one of $R_6$, and $R_7$ is $CH_3$.

9. The compound of claim 1, wherein at least one of $R_1$ and $R_2$ is Cl, at least one of $R_3$, $R_4$, and $R_5$ is $CH_3$, and at least one of $R_6$, and $R_7$ is $CH_3$.

10. The compound of claim 1, wherein $R_1$ and $R_2$ are Cl, and $R_3$ and $R_4$ are $CH_3$.

11. The compound of claim 1, wherein $R_1$ and $R_2$ are Cl, and $R_6$ and $R_7$ are $CH_3$.

12. The compound of claim 1, wherein $R_3$ and $R_4$ are $CH_3$, and $R_6$, and $R_7$ are $CH_3$.

13. The compound of claim 1, wherein $R_1$ and $R_2$ are Cl, and $R_3$ and $R_4$ are $CH_3$, and $R_6$ and $R_7$ are $CH_3$.

14. The compound of claim 1, wherein $R_1$ and $R_2$ are Cl, and $R_3$, $R_4$, $R_5$, $R_6$, and $R_7$ are $CH_3$.

15. A composition, comprising the compound of claim 1 disposed in a pharmaceutically-acceptable carrier, vehicle, or diluent.

* * * * *

UNITED STATES PATENT AND TRADEMARK OFFICE
CERTIFICATE OF CORRECTION

PATENT NO. : 10,519,108 B2
APPLICATION NO. : 15/758555
DATED : December 31, 2019
INVENTOR(S) : Jody A. Summers et al.

Page 1 of 1

It is certified that error appears in the above-identified patent and that said Letters Patent is hereby corrected as shown below:

In the Specification

Column 1, Line 16, after the paragraph entitled Cross-Reference to Related Applications, and before Background, insert the following header and paragraph:
--STATEMENT REGARDING FEDERALLY
SPONSORED RESEARCH OR DEVELOPMENT
This invention was made with government support under Contract Number EY009391 awarded by the National Institutes of Health. The government has certain rights in the invention.--

Signed and Sealed this
Eighteenth Day of August, 2020

Andrei Iancu
*Director of the United States Patent and Trademark Office*